US009138465B2

(12) United States Patent
Ozono et al.

(10) Patent No.: US 9,138,465 B2
(45) Date of Patent: Sep. 22, 2015

(54) PHARMACEUTICAL COMPOSITION FOR TREATING LYSOSOMAL STORAGE DISEASE

(75) Inventors: Keiichi Ozono, Abeno-ku (JP); Takanobu Otomo, Toyonaka (JP); Norio Sakai, Neyagawa (JP)

(73) Assignee: OSAKA UNIVERSITY, Osaka (JP)

( * ) Notice: Subject to any disclaimer, the term of this patent is extended or adjusted under 35 U.S.C. 154(b) by 32 days.

(21) Appl. No.: 14/114,122

(22) PCT Filed: Apr. 27, 2012

(86) PCT No.: PCT/JP2012/061405
§ 371 (c)(1),
(2), (4) Date: Oct. 25, 2013

(87) PCT Pub. No.: WO2012/147933
PCT Pub. Date: Nov. 1, 2012

(65) Prior Publication Data
US 2014/0044694 A1  Feb. 13, 2014

(30) Foreign Application Priority Data

Apr. 28, 2011 (JP) ................................. 2011-101560

(51) Int. Cl.
A61K 38/54 (2006.01)
A61K 38/47 (2006.01)
A61K 38/48 (2006.01)
C12N 5/07 (2010.01)

(52) U.S. Cl.
CPC ................ *A61K 38/47* (2013.01); *A61K 38/48* (2013.01); *A61K 38/488* (2013.01); *A61K 38/4813* (2013.01); *C12N 5/06* (2013.01); *C12Y 302/0102* (2013.01); *C12Y 302/01021* (2013.01); *C12Y 302/01022* (2013.01); *C12Y 302/01023* (2013.01); *C12Y 302/01024* (2013.01); *C12Y 302/01031* (2013.01); *C12Y 302/01046* (2013.01); *C12Y 302/01051* (2013.01); *C12Y 302/01052* (2013.01); *C12Y 304/14001* (2013.01); *C12Y 304/16005* (2013.01); *C12Y 304/22001* (2013.01); *C12Y 304/22038* (2013.01); *C12Y 304/23005* (2013.01); *C12Y 304/23034* (2013.01)

(58) Field of Classification Search
None
See application file for complete search history.

(56) References Cited

U.S. PATENT DOCUMENTS

| 6,670,165 | B2 | 12/2003 | Canfield |
| 2002/0150981 | A1 | 10/2002 | Canfield |
| 2003/0119088 | A1 | 6/2003 | Canfield et al. |
| 2005/0064539 | A1 | 3/2005 | Chiba et al. |
| 2006/0110793 | A1 | 5/2006 | Goldenberg et al. |
| 2007/0009500 | A1 | 1/2007 | Blazar et al. |
| 2007/0015250 | A1 | 1/2007 | Goldenberg et al. |
| 2008/0014188 | A1 | 1/2008 | Zankel et al. |
| 2009/0111143 | A1 | 4/2009 | Goldenberg et al. |
| 2009/0191178 | A1 | 7/2009 | Zankel et al. |
| 2009/0253179 | A1 | 10/2009 | Goldenberg et al. |
| 2010/0311162 | A1 | 12/2010 | Goldenberg et al. |
| 2011/0236404 | A1 | 9/2011 | Goldenberg et al. |
| 2011/0268750 | A1 | 11/2011 | Mamoun et al. |

FOREIGN PATENT DOCUMENTS

| JP | 2002-369692 A | 12/2002 |
| JP | 2003-509043 A | 3/2003 |
| JP | 2005-516594 A | 6/2005 |
| JP | 2007-513188 A | 5/2007 |
| JP | 2007-523648 A | 8/2007 |
| JP | 2008-507300 A | 3/2008 |
| JP | 2009-108004 A | 5/2009 |
| WO | 2009-115561 A1 | 9/2009 |
| WO | 2011/000958 A1 | 1/2011 |

OTHER PUBLICATIONS

Michihara, A., Toda, K., Kubo, T., Fujiwara, Y., Akasaki, K., and Tsuji, H. "Disruptive Effect of Chloroquine on Lysosomes in Cultured Rat Hepatocytes", Biol. Pharm. Bull. 2005, vol. 28, pp. 947-951.*

Oda, K., Nishimura, Y., Ikehara, Y., and Kato, K. "Bafilomycin A1 inhibits the targeting of lysosomal acid hydrolases in cultured hepatocytes", Biochem Biophys Res Commun 1991, vol. 178, pp. 369-377.*

Gasa, S., "The defeficiency of UDP-GlcNAc: lysosomal enzyme Alpha-N-acetylglucosaminylphosphotransferase and the related diseases", Protein, nucleic acid and enzyme, 1998, vol. 33, No. 5, pp. 706-707.

Hasilik A., et al., "Biosynthesis of Lysosomal Enzymes in Fibroblasts", The Journal of Biological Chemistry, 1980, vol. 255, No. 10, p. 4946-4950.

International Preliminary Report on Patentability issued in PCT/JP2012/061405.

(Continued)

*Primary Examiner* — Allison Fox
*Assistant Examiner* — Michelle F Paguio Frising
(74) *Attorney, Agent, or Firm* — Sughrue Mion, PLLC

(57) ABSTRACT

The purpose of the present invention is to provide, in a simple and also inexpensive manner, a pharmaceutical composition which comprises a plurality of lysosomal enzymes and is effective in treating lysosomal storage disease caused by a deficiency in a plurality of lysosomal enzymes. Provided is a pharmaceutical composition for treating lysosomal storage disease, the composition comprising as an active ingredient a lysosomal enzyme group obtained from cells derived from a subject who does not suffer from lysosomal storage disease.

3 Claims, 7 Drawing Sheets

(56) References Cited

OTHER PUBLICATIONS

Milunsky, A. et al., "Lysosomal Enzyme Variations in Cultured Normal Skin Fibroblasts", Life Sciences, 1972, vol. 11, No. 22, Part II, p. 1101-1107.

Miranda S. R. P., et al., "Infusion of recombinant human acid sphingomyelinase into Niemann-Pick disease mice leads to visceral, but not neurological, correction of the pathophysiology", FASEB Journal, 2000, vol. 14, p. 1988-1995.

Reczek, D., et al., "LIMP-2 Is a Receptor for Lysosomal Mannose-6-Phosphate-Independent Targeting of β-Glucocerebrosidase", Cell 131, pp. 770-783, 2007.

Sardiello M., et al., "A Gene Network Regulating Lysosomal Biogenesis and Function", Science 325, p. 473-477 (2009).

Takada. G., and Takahashi, T., "Enzyme Replacement Therapy", Japanese Journal of Clinical Medicine, 1995, vol. 53, No. 12, p. 197-202.

* cited by examiner

[Fig. 5]
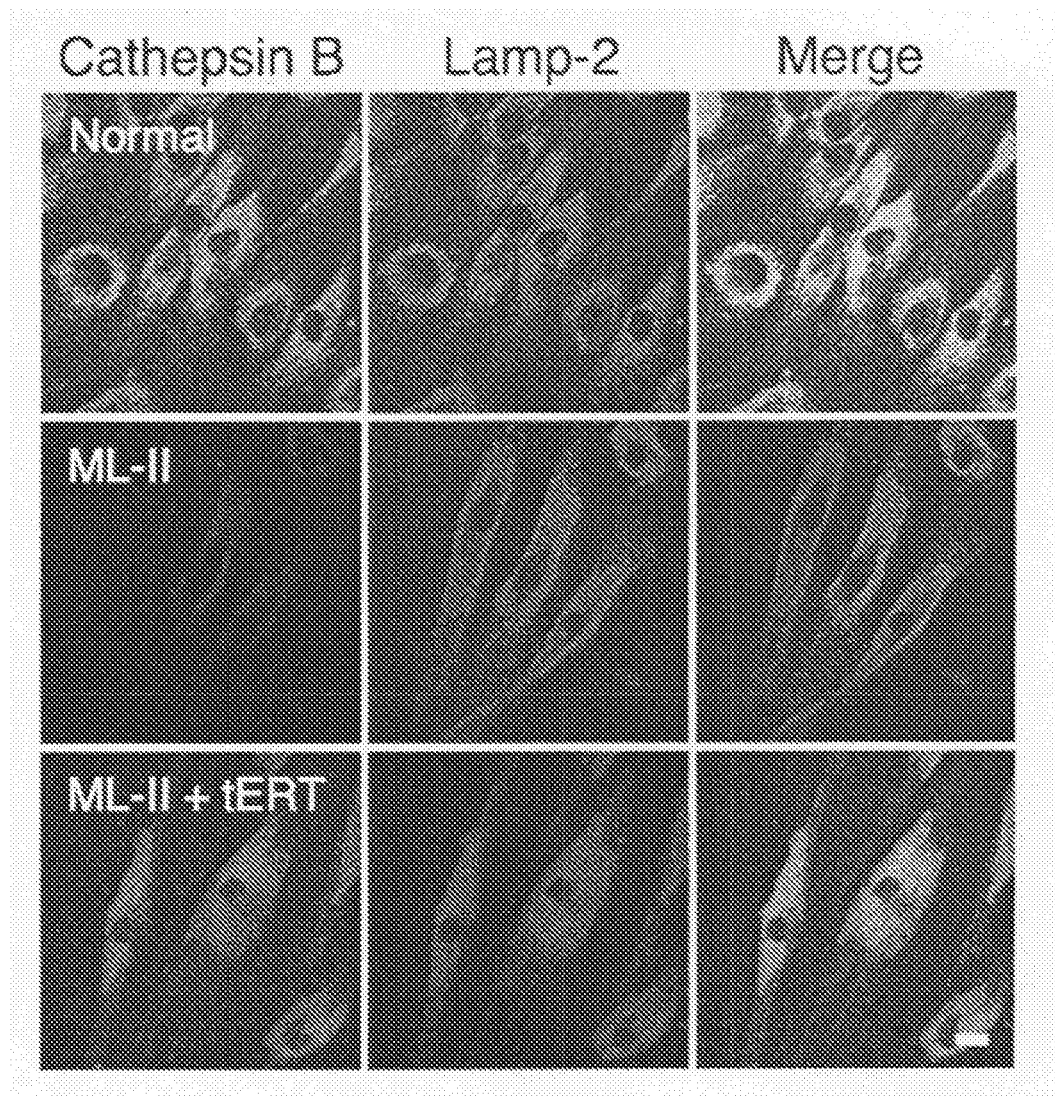

PHARMACEUTICAL COMPOSITION FOR TREATING LYSOSOMAL STORAGE DISEASE

CROSS REFERENCE TO RELATED APPLICATIONS

This is a National Stage of International Application No. PCT/JP2012/061405, filed Apr. 27, 2012, claiming priority from Japanese Patent Application No. 2011-101560, filed Apr. 28, 2011, the contents of all of which are incorporated herein by reference in their entirety.

TECHNICAL FIELD

The present invention relates to a pharmaceutical composition for treating a lysosomal disease.

BACKGROUND ART

A lysosome is a cellular organelle. Various materials (foreign materials, waste materials, etc.) in a cell are broken down by action of lysosomal enzymes present in a lysosome. It is known that there are more than 50 kinds of lysosomal enzymes. Lysosomal enzymes optimally work at a pH in an acidic environment. A deficiency of a lysosomal enzyme due to a genetic defect causes accumulation of a substrate in a cell, which leads to a lysosomal disease. At present, more than 40 kinds of such congenital lysosomal diseases are known. However, a fundamental therapeutic method has not been found yet.

Lysosomal diseases have been treated by making up for the deficient enzymes, and for this purpose, enzyme replacement therapy, bone marrow transplantation, and gene therapy have been attempted. To date, lots of lysosomal enzymes have been identified and linked with lysosomal diseases.

For enzyme replacement therapy, a recombinant enzyme has been developed using a cell line strongly expressing one particular lysosomal enzyme. To date, 7 kinds of enzyme preparations comprising such a single recombinant lysosomal enzyme have been marketed, i.e., a Gaucher's disease therapeutic agent, CEREZYME (registered trade mark) (a recombinant imiglucerase preparation); a Fabry disease therapeutic agent, FABRAZYME (registered trade mark) (a recombinant agalsidase beta preparation); a Fabry disease therapeutic agent, REPLAGAL (registered trade mark) (a recombinant agalsidase alfa preparation); a mucopolysaccharidosis type I therapeutic agent, ALDURAZYME (registered trade mark) (a recombinant laronidase preparation); a mucopolysaccharidosis type II therapeutic agent, MYOZYME (registered trade mark) (a recombinant alglucosidase alfa preparation); a mucopolysaccharidosis type II therapeutic agent, ELAPRASE (registered trade mark) (a recombinant idursulfase preparation); and a mucopolysaccharidosis type VI therapeutic agent, NAGLAZYME (registered trade mark) (a recombinant galsulfase preparation).

However, these therapeutic agents are directed to treat lysosomal diseases caused by a deficiency of a single lysosomal enzyme, and are not effective against lysosomal diseases caused by deficiencies of two or more lysosomal enzymes. In addition, the above-mentioned therapeutic agents which are currently marketed are very expensive. Therefore, there is a need for development of inexpensive therapeutic agents.

It is known that a mannose 6-phosphate residue is added to lysosomal enzymes when they are synthesized within a cell, and thereby they are transported via a mannose 6-phosphate receptor to a lysosome.

Based on this fact, for the purpose of effective delivery of an enzyme to a lysosome in an enzyme replacement therapy, some studies to obtain highly-phosphorylated lysosomal enzymes have been conducted. For example, a method of modifying an isolated lysosomal enzyme with a mannose 6-phosphate residue (see Patent Literature 1), and a method of preparing a highly-phosphorylated recombinant lysosomal enzyme using a special cell line (see Patent Literature 2) are reported. However, using these techniques, it is difficult to produce many kinds of lysosomal enzymes at once and inexpensively.

Examples of lysosomal diseases caused by deficiencies of two or more lysosomal enzymes include mucolipidosis type II (hereinafter, referred to as "ML-II"), and mucolipidosis type III (hereinafter, referred to as "ML-III") which is a mild type of ML-II. These lysosomal diseases are caused by a defect in GlcNAc-phosphotransferase, which adds a mannose 6-phosohate residue to lysosomal enzymes synthesized in a cell. In ML-II and ML-III, a mannose 6-phosohate residue is not added to lysosomal enzymes synthesized in the cell due to a defect in GlcNAc-phosphotransferase, and therefore the lysosomal enzymes are not recognized by a mannose 6-phosphate receptor and then are not transported to lysosomes. Thus, patients with ML-II and ML-III have deficiencies of almost all of lysosomal enzymes in lysosomes.

Therefore, administration of a single enzyme preparation as mentioned above is not effective for the treatment of ML-II and ML-III. For the treatment of ML-II and ML-III, it is theoretically necessary to replace all of the deficient lysosomal enzymes. However, it is very difficult to isolate and purify all of more than 50 kinds of lysosomal enzymes individually in which ML-II and ML-III patients are deficient. In addition, recombinant lysosomal enzyme preparations as mentioned above are very expensive. It is also economically difficult to use several tens of the expensive enzyme preparations.

Under such circumstances, conventional enzyme preparations using single recombinant lysosomal enzymes cannot be applied to the treatment of such lysosomal diseases as ML-II and ML-III. Therefore, new useful therapeutic agents for lysosomal diseases are desired.

CITATION LIST

Patent Literatures

Patent Literature 1: JP-A 2003-509043
Patent Literature 2: JP-A 2007-523648

DISCLOSURE OF INVENTION

Problems to be Solved by the Invention

An object of the present invention is to provide simply and inexpensively a pharmaceutical composition comprising two or more lysosomal enzymes which is effective against a lysosomal disease caused by deficiencies of two or more lysosomal enzymes.

Solutions to the Problems

The inventors of the present invention intensively studied for solving the above problems. As a result, they found that many kinds of lysosomal enzymes in a state of being modified with a mannose 6-phosphate residue could be obtained at once by adding a specific reagent such as ammonium chloride to a cell derived from a subject which/who does not suffer from a lysosomal disease, culturing the cell, and collecting and then purifying a culture supernatant. They also found that the many kinds of lysosomal enzymes thus obtained could be utilized as therapeutic agents for lysosomal diseases. Thus, the present invention was completed.

That is, the present invention provides:

(1) A pharmaceutical composition for treating a lysosomal disease, comprising a group of lysosomal enzymes as an active ingredient, wherein the group of lysosomal enzymes is obtained by culturing a cell;

(2) The pharmaceutical composition according to (1), wherein the cell has the ability to add a mannose 6-phosphate residue to lysosomal enzymes;

(3) The pharmaceutical composition according to (1), wherein the cell is derived from a subject not suffering from lysosomal disease;

(4) The pharmaceutical composition according to any one of (1) to (3), wherein the group of lysosomal enzymes is obtained by a method comprising the following steps:

adding to the cell one or more reagents selected from the group consisting of amphiphilic amines, lysosome-tropic amines, ionophores, and V-ATPase inhibitors, followed by culturing;

collecting a culture supernatant; and purifying and/or concentrating the obtained culture supernatant;

(5) The pharmaceutical composition according to (4), wherein the reagent(s) is selected from the group consisting of ammonium chloride, chloroquine, monencin, nigericin, and bafilomycin A1;

(6) The pharmaceutical composition according to any one of (1) to (5), wherein the cell is selected from the group consisting of a normal skin fibroblast, a COS-1 cell, an NIH3T3 cell, an HEK293 cell, a HeLa cell, and a CHO cell;

(7) The pharmaceutical composition according to any one of (1) to (6), wherein the lysosomal enzyme is not a recombinant enzyme;

(8) The pharmaceutical composition according to any one of (1) to (7), wherein the group of lysosomal enzymes comprises a lysosomal enzyme having a mannose 6-phosphate residue; and (9) The pharmaceutical composition according to any one of (1) to (8), for treating mucolipidosis type II or type III.

In a further aspect, the present invention provides a method of preparing a group of lysosomal enzymes, which comprising adding to a cell a reagent selected from the group consisting of amphiphilic amines, lysosome-tropic amines, ionophores, and V-ATPase inhibitors, followed by culturing, and collecting a culture supernatant.

In another aspect, the present invention provides use of a group of lysosomal enzymes for treatment of a lysosomal disease, wherein the group of lysosomal enzymes is obtained by culturing a cell.

In yet another aspect, the present invention provides a method of treating a lysosomal disease which comprises administering a group of lysosomal enzymes to a patient, wherein the group of lysosomal enzymes is obtained by culturing a cell.

In yet another aspect, the present invention provides use of a group of lysosomal enzymes for manufacture of a pharmaceutical composition for treating a lysosomal disease, wherein the group of lysosomal enzymes is obtained by culturing a cell.

Effects of the Invention

According to the present invention, a pharmaceutical composition comprising two or more lysosomal enzymes which is effective against a lysosomal disease caused by deficiencies or reduced activities of two or more lysosomal enzymes can be obtained simply and inexpensively.

BRIEF DESCRIPTION OF DRAWINGS

FIG. 4-1 displays graphs showing results of a competitive inhibition test between lysosomal enzymes and mannose 6-phosphate. The unit of enzyme activity is "nmol/h/mg protein".

FIG. 4-2 displays graphs showing results of a competitive inhibition test between lysosomal enzymes and mannose 6-phosphate. The unit of enzyme activity is "nmol/h/mg protein".

FIG. 5 displays fluorescence micrographs showing intracellular distribution of lysosomal enzymes. "Lamp-2" means a marker for lysosome. "Merge" shows images obtained by laying an image of cathepsin B on an image of Lamp-2. "ML-II+tERT" means a cell from an ML-II patient which is treated with tERT.

MODE FOR CARRYING OUT THE INVENTION

Figure 1:
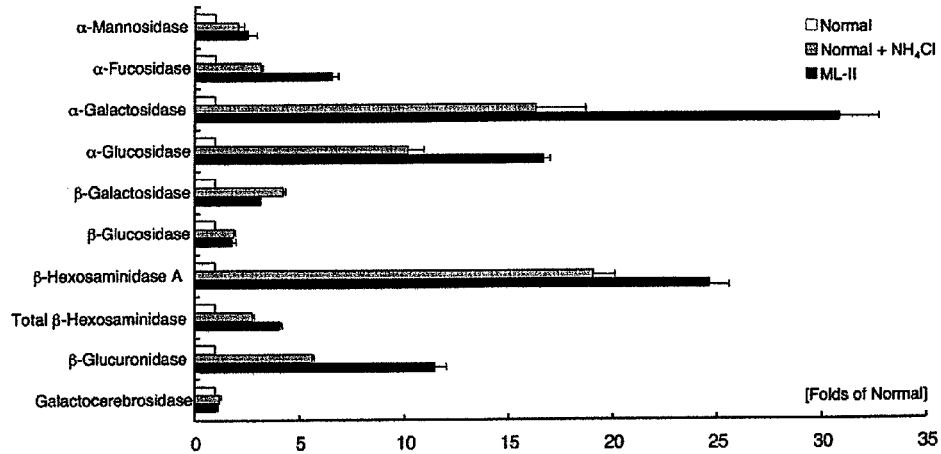
FIG. 1 is a graph showing activity of each lysosomal enzyme in a cell culture supernatant. Each enzyme activity is expressed as a rate (-fold) relative to the enzyme activity in a culture supernatant of a normal cell. "Normal" means a culture supernatant of a normal cell. "ML-II" means a culture supernatant of a cell from a patient with ML-II.

In the present invention, one kind of cell may be cultured to obtain a group of lysosomal enzymes, or two or more kinds of cells may be cultured to obtain a group of lysosomal enzymes. In particular, according to the present invention, even when one kind of cell is cultured, many kinds of lysosomal enzymes can be sufficiently obtained.

Preferred examples of the cell to be used in the present invention include a cell having the ability to add a mannose 6-phosphate residue to lysosomal enzymes, and a cell derived from a subject who/which does not suffer from a lysosomal disease.

Examples of the "cell having the ability to add a mannose 6-phosphate residue" as used herein include a cell derived from a subject who/which does not suffer from a disease caused by an abnormality of GlcNAc-phosphotransferase, and a cell having normal GlcNAc-phosphotransferase.

The "cell derived from a subject who/which does not suffer from a lysosomal disease" as used herein means a normal cell derived from a healthy subject, and a cell derived from a subject suffering from a disease other than lysosomal diseases, but not suffering from lysosomal diseases.

The subject is a mammalian subject, such as a human, a monkey, a bovine, a canine, a feline, a mouse, a rat, a hamster, a rabbit, a marmoset, a sheep, a goat, etc., and it is preferably a human.

The cell to be used in the present invention may be a mutant cell or a cell that is not a mutant. The "mutant" as used herein includes a natural mutant, and an artificial gene recombinant. An example of the mutant cell includes a cell having increased expression amounts of lysosomal enzymes which is obtained by introduction of TFEB (Science 325, 473-477, 2009) by gene recombination technology.

The cell to be used in the present invention may be a commercially available cell, or may be a cell directly obtained from the above-mentioned subject. The cell to be used in the present invention may also be a commonly available cultured cell, such as an established cell line or a deposited cell line.

Examples of the cell to be used in the present invention include, but not limited to, cells derived from skin, kidney, embryo, ovary, uterus, etc., preferably a skin fibroblast, a kidney fibroblast, and an embryo fibroblast, more preferably a normal skin fibroblast, a COS-1 cell, an NIH3T3 cell, an HEK293 cell, a HeLa cell, and a CHO cell, and still more preferably a normal human fibroblast.

The pharmaceutical composition of the present invention comprises a group of lysosomal enzymes obtained from a culture of the above-mentioned cell (hereinafter, referred to as "the lysosomal enzyme group of the present invention").

The lysosomal enzyme group of the present invention is an enzyme mixture consisting of two or more kinds of lysosomal enzymes which is obtained by culturing the above-mentioned cell, and comprises lysosomal enzymes having mannose 6-phoshohate residues.

The lysosomal enzyme group of the present invention consists of for example 5 or more kinds, 8 or more kinds, or 12 or more kinds of lysosomal enzymes, preferably 20 or more kinds of lysosomal enzymes, more preferably 30 or more kinds of lysosomal enzymes, still more preferably 40 or more kinds of lysosomal enzymes, and most preferably 50 or more kinds of lysosomal enzymes.

Preferably, lysosomal enzymes contained in the lysosomal enzyme group of the present invention are not recombinant enzymes and are wild-type enzymes. The "recombinant enzyme" as used herein refers to an enzyme produced in a host cell into which a gene encoding the enzyme has been integrated by gene recombination technology. The "wild-type enzyme" as used herein refers to an enzyme that the cell originally possesses. When lysosomal enzymes are wild-type, administration of the lysosomal enzyme group to the human body is safer.

Examples of lysosomal enzymes contained in the lysosomal enzyme group of the present invention include two or more kinds of enzymes selected from the group consisting of α-mannosidase, α-fucosidase, α-galactosidase, α-glucosidase, β-galactosidase, β-glucosidase, β-hexosaminidase (for example, β-hexosaminidase A, β-hexosaminidase B, β-hexosaminidase S), β-glucuronidase, galactocerebrosidase, cathepsin (for example, cathepsin A, cathepsin B, cathepsin C, cathepsin D, cathepsin E, cathepsin K, etc.), α-L-iduronidase, arylsulfatase, N-acetylgalactosamine-6-sulfatase, iduronate 2-sulfatase, heparan N-sulfatase, α-N-acetylglucosaminidase, acetylCoA-α-glucosaminide N-acetyltransferase, N-acetylglucosamine-6-sulfatase, galactose-6-sulfatase, arylsulfatase A, B and C, arylsulfatase A cerebroside, α-N-acetylgalactosaminidase, α-neuramidase, aspartylglucosaminidase, acid lipase, acid ceramidase, sphingomyelinase, palmitoyl-protein thioesterase, tripeptidyl peptidase, β-mannosidase, etc.

The lysosomal enzyme group of the present invention comprises preferably at least α-mannosidase, α-fucosidase, α-galactosidase, α-glucosidase, β-galactosidase, β-glucosidase, β-hexosaminidase, β-glucuronidase, galactocerebrosidase, and cathepsin, and more preferably at least α-mannosidase, α-fucosidase, α-galactosidase, α-glucosidase, β-galactosidase, β-glucosidase, β-hexosaminidase A, β-hexosaminidase B, β-glucuronidase, galactocerebrosidase, cathepsin B, and cathepsin D. Most preferably, the lysosomal enzyme group of the present invention comprises all kinds of lysosomal enzymes contained in the lysosome of a normal cell.

The lysosomal enzyme group of the present invention can be obtained from a culture of the above-mentioned cell by a known means or method. The lysosomal enzyme group of the present invention can be preferably obtained by addition of a suitable reagent (hereinafter, referred to as "the reagent for enzyme extraction") such as ammonium chloride to the above-mentioned cell, culture of the cell, and then purification and/or concentration of the obtained culture supernatant by a known means or method.

For example, the lysosomal enzyme group of the present invention can be obtained by culture of a cell derived from a subject who/which does not suffer from a lysosomal disease, and then extraction of lysosomal enzymes from the obtained cell by a known means or method. Preferably, the lysosomal enzyme group of the present invention is obtained by a method which comprises adding the suitable reagent for enzyme extraction to a cell derived from a subject who/which does not suffer from a lysosomal disease, culturing the cell, collecting a culture supernatant, and purifying and/or concentrating the obtained culture supernatant.

The culture conditions for the cell culture as described above, such as the composition of a culture medium, the temperature of a culture medium, the culture time, etc., may be selected as appropriate depending on the kind or amount of a cell to be used.

The reagent for enzyme extraction to be added to the cell may be any reagent as long as it allows the cell to excrete lysosomal enzymes contained in the lysosome of the cell into a culture supernatant. Examples of the reagent for enzyme extraction include amphiphilic amines, for example ammonium chloride; lysosome-tropic amines, for example chloroquine; ionophores, for example monencin and nigericin; and V-ATPase inhibitors, for example bafilomycin A1. One or more kinds of the reagents for enzyme extraction may be added to the cell. Preferably, one or more kinds of reagents selected from the group consisting of ammonium chloride, chloroquine, monencin, nigericin, and bafilomycin A1 are added to the cell. More preferably, one or more kinds of reagents selected from the group consisting of ammonium chloride, chloroquine, and bafilomycin A1 are added to the cell.

The present invention provides, for the first time, an attempt to use a group of lysosomal enzymes obtained by addition of the reagent as described above to a cell and then culture of the cell in the treatment of lysosomal diseases.

The amount of the reagent for enzyme extraction is not particularly limited as long as it allows lysosomal enzymes to be excreted from a lysosome. For example, in the case of ammonium chloride, it may be used at a concentration of 15 mM or more in a culture medium, for example at about 20 mM in a culture medium. For example, in the case of chloroquine, it may be used at a concentration of 15 µM or more in a culture medium, for example at about 20 µM in a culture medium. For example, in the case of bafilomycin A1, it may be used at a concentration of 15 nM or more in a culture medium, for example at about 20 nM in a culture medium.

After the reagent for enzyme extraction is added to a cell, the cell is cultured and then a culture supernatant is obtained. A culture period after addition of the reagent is not particularly limited as long as adequate amounts of lysosomal enzymes are excreted into the culture supernatant during the period. The cell is usually cultured for several days, for example, for 3 days, for 5 days, for 7 days, for 10 days, for 14 days or more.

The culture supernatant may be collected by a conventional method. Examples of a collection method include filtration and centrifugation. After collection of the culture supernatant, the reagent for enzyme extraction and impurities are removed by purification.

The culture supernatant may be purified by a conventional method. Examples of a purification method include extraction with a solvent, precipitation with a organic solvent, filtration such as ultrafiltration, affinity chromatography such as affinity chromatography with a mannose 6-phosphate receptor column or a mannose 6-phosphate antibody, chromatography such as hydrophobic chromatography or ion-exchange chromatography, and salting-out.

The culture supernatant may be concentrated by a conventional method. Examples of a concentration method include ultrafiltration and salting-out.

The culture supernatant may be purified and/or concentrated to the desired extent as appropriate.

The lysosomal enzyme group of the present invention thus obtained contains many kinds of lysosomal enzymes contained in the lysosome of the cultured cell, preferably all kinds of lysosomal enzymes contained in the lysosome of the cultured cell.

Since the lysosomal enzyme group of the present invention is obtained by excretion of normal lysosomal enzymes that already exist in a lysosome from the lysosome, the lysosomal enzyme group can contain lysosomal enzymes in a state of being modified with a mannose 6-phosphate residue.

Therefore, according to the present invention, many kinds of lysosomal enzymes having mannose 6-phosphate residues can be obtained at once without requiring a step of adding a mannose 6-phosphate residue, and can be easily used in the treatment of lysosomal diseases.

The pharmaceutical composition of the present invention may be the lysosomal enzyme group of the present invention as it is, or can be in a suitable dosage form, such as an injection, a tablet, a capsule, a granule, a fine granule, a powder or the like, with a pharmaceutically acceptable carrier, an additive such as a stabilizer, a buffering agent, a filler, a binder, a disintegrant, a corrigent, a colorant, a flavor or the like, or an excipient. Examples of the pharmaceutically acceptable carrier include physiological saline, dextrose, glycerol, animal fat, and vegetable oil. In particular, water, physiological saline, dextrose, and glycerol are preferably used as a carrier for an injection.

The pharmaceutical composition of the present invention can be administered, for example, orally or parenterally, for example by intravenous injection, intraventricular injection, intraperitoneal injection, intramuscular injection or the like, or transdermally. The dosage amount of the pharmaceutical composition of the present invention can be determined depending on the age, body weight, or symptom of a patient, the route of administration, or the like.

Since the lysosomal enzymes contained in the lysosomal enzyme group of the present invention are modified with mannose 6-phosphate residues, the lysosomal enzymes are incorporated into the cells and lysosomes of a subject after they are administered to the subject.

Since the lysosomal enzyme group of the present invention contains many kinds of lysosomal enzymes, the pharmaceutical composition of the present invention is effective against lysosomal diseases caused by a deficiency or reduced activity of single lysosomal enzyme and lysosomal diseases caused by deficiencies or reduced activities of two or more lysosomal enzymes. The pharmaceutical composition of the present invention is particularly effective in the treatment of mucolipidosis type II and mucolipidosis type III.

Examples of lysosomal diseases to be treated with the pharmaceutical composition of the present invention include, but not limited to, aspartylglycosaminuria, Fabry's disease, infantile Batten's disease (CNL1), classical late-onset infantile Batten's disease (CNL2), Farber's disease, fucosidosis, galactosialidosis, Gaucher's disease type 1, type 2 and type 3, $G_{M1}$-gangliosidosis, Hunter syndrome, Hurler syndrome, Hurler-Scheie syndrome, Scheie syndrome, Krabbe disease, α-mannosidosis, β-mannosidosis, Maroteaux-Lamy syndrome, metachromatic leukodystrophy, Morquio syndrome type A, Morquio syndrome type B, mucolipidosis type II/III, Niemann-Pick disease type A and type B, Pompe disease, Sandhoff's disease, Sanfilippo syndrome type A, Sanfilippo syndrome type B, Sanfilippo syndrome type C, Sanfilippo syndrome type D, Schindler disease, Schindler Kanzaki disease, sialidosis, Sly syndrome, Tay-Sachs disease, Wolman disease, mucopolysaccharidosis type IX, multiple sulfatase deficiency, Danon disease, free sialic acid storage disease, and ceroid lipofuscinosis. The pharmaceutical composition of the present invention is preferably used for the treatment of mucolipidosis type II and mucolipidosis type III.

The lysosomal enzyme group of the present invention can be further purified and then used for production of a single enzyme preparation.

The lysosomal enzyme group of the present invention can be also used as a lysosomal enzyme reagent for research.

Hereinafter, the present invention is explained by way of Examples, which the present invention is not limited to.

Example 1

Preparation of Lysosomal Enzyme Group

In a culture dish with a diameter of 10 cm, a normal skin fibroblast was cultured in a DMEM medium containing 10% FBS (fetal bovine serum) and a recommended amount of an antibiotic and/or an antibacterial agent [Gibco (registered trade name) Antibiotic-Antimycotic, Life Technologies] (hereinafter, referred to as "a standard culture medium") until the cell became confluent. To the cultured normal skin fibroblast, ammonium chloride was added in such an amount that the concentration of ammonium chloride became 20 mM in the culture medium. Then, the cell was cultured. Seven days after, a culture supernatant was collected, and filtered with a 0.2 μm sterilizing filter to remove large debris and living cells. After the filtration, the activities of lysosomal enzymes contained in the supernatant were measured by a method as described later.

Then, the culture supernatant was centrifuged at 0° C. in a spin column having a filter with a molecular weight cutoff value of 5000 (Vivaspin 15R, Sartorius Stedim Biotech GmbH) to remove ammonium chloride. A group of lysosomal enzymes thus obtained was finally diluted with serum-free DMEM so that the α-mannosidase activity became 600 nmol/h/μL, and then used as a sample in the Examples described later. At the point of use, the sample had the following enzyme activities: 364.6 nmol/h/μL of α-mannosidase, 38.4 nmol/h/μL of α-fucosidase, 5.6 nmol/h/μL of α-galactosidase, 10.3 nmol/h/μL of α-glucosidase, 35.0 nmol/h/μL of β-galactosidase, 25.9 nmol/h/μL of β-glucosidase, 2650.4 nmol/h/μL of total β-hexosaminidase, 522.9 nmol/h/μL of β-hexosaminidase A, 14.3 nmol/h/μL of β-glucuronidase, and 0.57 nmol/h/μL of galactocerebrosidase. The enzyme activities were measured according to a method as described later.

In the Examples described later, tERT was performed by culture of a cell for 7 days after addition of the sample to a culture medium. After that, the culture medium was replaced with a normal standard culture medium, and then, each assay was performed within 24 hours.

Measurement of Enzyme Activity in Lysosomal Enzyme Group

To confirm that the lysosomal enzyme group thus obtained contained lysosomal enzymes, the culture supernatant obtained after addition of ammonium chloride and culture was subjected to measurement of the activities of lysosomal enzymes. As controls, a culture supernatant of a normal skin fibroblast that was cultured without addition of ammonium chloride, and a culture supernatant of an ML-II patient-derived skin fibroblast (hereinafter, referred to as "an ML-II cell") that was cultured without addition of ammonium chloride were used to measure the activities of lysosomal enzymes in the culture supernatant.

The activities of lysosomal enzymes were measured by a standard method using an artificial 4-methylumbelliferyl substrate. Briefly, a sample was incubated with the artificial substrate at 37° C. for 1 hour in an acidic phosphate or citrate buffer, and fluorescence was measured on a microplate reader at an excitation wavelength of 365 nm and an emission wavelength of 450 nm. For galactocerebrosidase, 6-hexadecanoylamino-4-methylumbelliferyl β-D-galactopyranoside (Slater and Frith Ltd.) was used as a substrate, and fluorescence was measured at an excitation wavelength of 385 nm and an emission wavelength of 450 nm. The enzyme activities were calculated as nmol/h/μL.

Results are shown in FIG. 1. In FIG. 1, each enzyme activity is expressed as a rate (-fold) relative to the enzyme activity in a culture supernatant of a normal cell.

Results

As seen from FIG. 1, the culture supernatant of the normal skin fibroblast with addition of ammonium chloride contained at least 10 kinds of lysosomal enzymes α-mannosidase, α-fucosidase, α-galactosidase, α-glucosidase, β-galactosidase, β-glucosidase, β-hexosaminidase A, β-hexosaminidase B, β-glucuronidase, and galactocerebrosidase). The pattern of enzyme activities in the culture supernatant of the normal skin fibroblast was very similar to the pattern of enzyme activities in the culture supernatant of the ML-II cell.

In the case of ML-II, lysosomal enzymes are not recognized by a mannose 6-phosphate receptor and not transported to lysosomes because a mannose 6-phosphate residue is not attached to lysosomal enzymes, and therefore the depletion of lysosomal enzymes in lysosomes is caused and the lysosomal enzymes having no mannose 6-phosphate residue are accumulated outside cells. Thus, a culture supernatant of an ML-II cell contains many kinds of lysosomal enzymes. This is consistent with the measurement results of the enzyme activities in the culture supernatant of the ML-II cell.

Example 2

Confirmation of Intracellular Uptake of Lysosomal Enzyme Group

The lysosomal enzyme group obtained in Example 1 was administered to an ML-II cell to perform tERT. The activities of lysosomal enzymes within the cell were measured to confirm that lysosomal enzymes in the active states were taken up by the cell.

The lysosomal enzyme group sample obtained in Example 1 was added to a culture medium of an ML-II cell, and the cell was cultured for a given period. Then, the cell was isolated from the culture medium, and sonicated in water containing a protease inhibitor to obtain a suspension. The protein concentration of the suspension was measured by a conventional method. The activities of lysosomal enzymes in the suspension were measured according to the method as described in Example 1. The enzyme activities were calculated as nmol/h/mg protein. As controls, a normal skin fibroblast, and an ML-II cell that was not treated with tERT were used.

Figure 2:
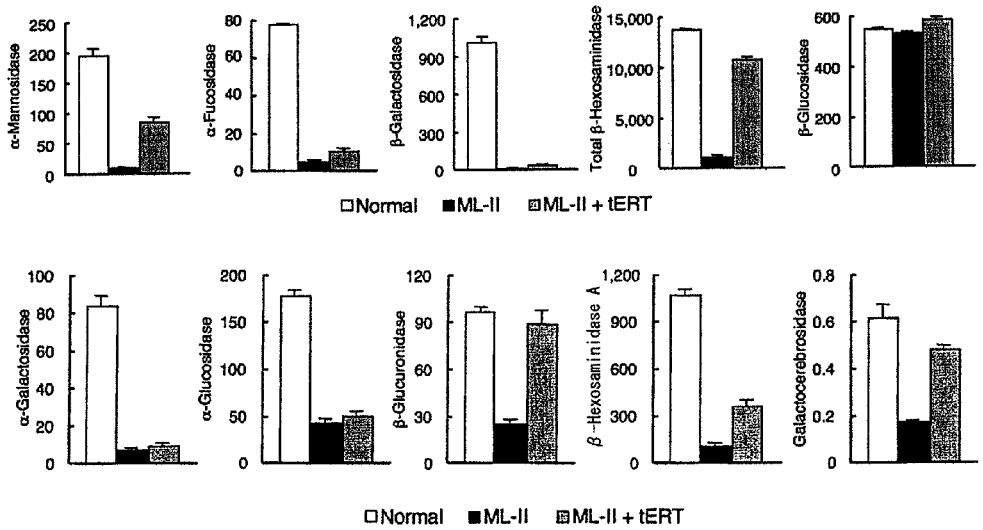
FIG. 2 displays graphs showing lysosomal enzyme activities within a cell. "Normal" means a normal cell. "ML-II" means a cell from a patient with ML-II. "ML-II+tERT" means a cell from an ML-II patient which is treated with total enzyme replacement therapy (hereinafter, referred to as tERT). The unit of enzyme activity is "nmol/h/mg protein".

Results are shown in FIG. 2.

As seen from FIG. 2, the activities of lysosomal enzymes within the cell were increased by tERT. Thus, it was found that lysosomal enzymes were taken up by the cell.

Figure 3:
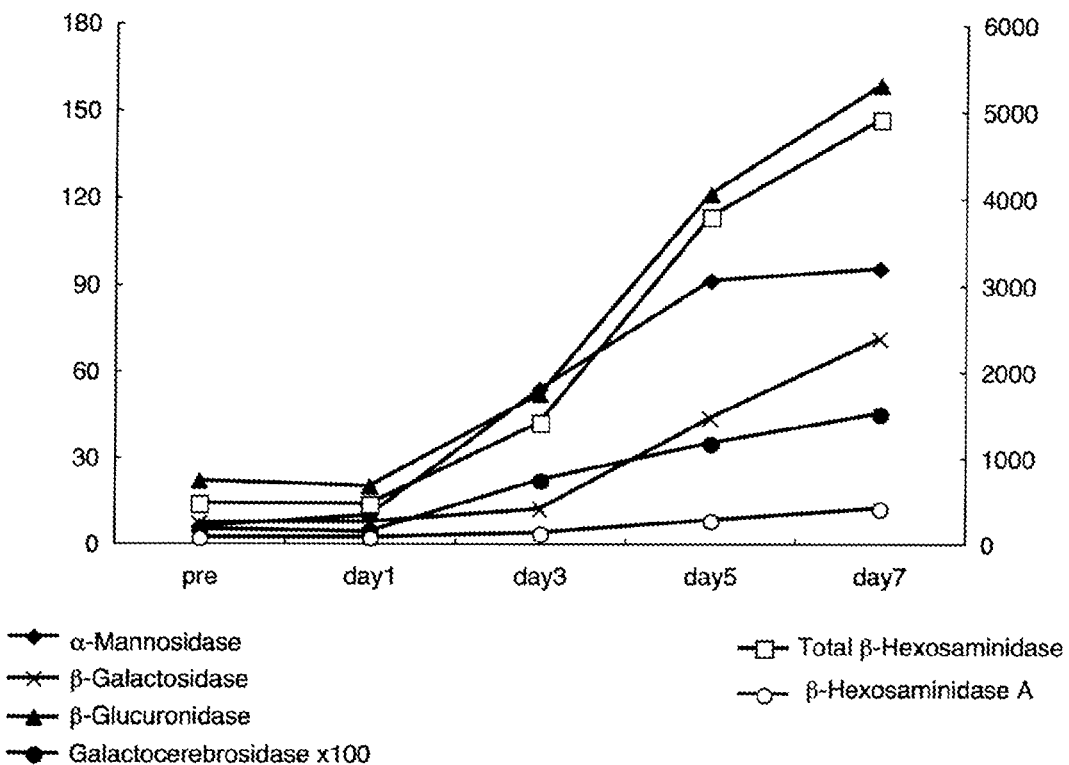
FIG. 3 is a graph showing intracellular uptake of lysosomal enzymes over time. The unit of enzyme activity is "nmol/h/mg protein". The horizontal axis indicates the number of days before and after addition of lysosomal enzymes. The left vertical axis indicates the enzyme activities of α-mannosidase, β-galactosidase, β-glucuronidase, and galactocerebrosidase. The right vertical axis indicates the enzyme activities of total β-hexosaminidase, and β-hexosaminidase A.

In addition, FIG. 3 shows uptake of lysosomal enzymes by the ML-II cell over time.

Lysosomal enzymes were continuously taken up by the cell for at least 7 days. The activities of lysosomal enzymes within the cell continued to increase for 7 days. Therefore, in this Example, the cells collected 7 days after the tERT treatment were used to perform the evaluation as described above. Also, in Examples 4-9 described later, the cells collected 7 days after the tERT treatment were used.

Example 3

Competitive Inhibition Test for Mannose 6-Phosphate

To confirm that the lysosomal enzyme group was taken up by a cell via a mannose 6-phosphate receptor on the cell surface, inhibition of intracellular uptake was tested by simultaneous administration of the lysosomal enzyme group and mannose 6-phosphate to a cell.

The lysosomal enzyme group sample obtained in Example 1 was added to a culture medium of an ML-II cell. At the same time, mannose 6-phosphate was not added (0 mM), or mannose 6-phosphate was added to the culture medium so that the concentration became 5 mM or 10 mM in the culture medium. The cell was cultured for a given period. Then, the activities of lysosomal enzymes within the cell were measured according to the methods as described in Example 1 and Example 2.

Figures 1, 4:
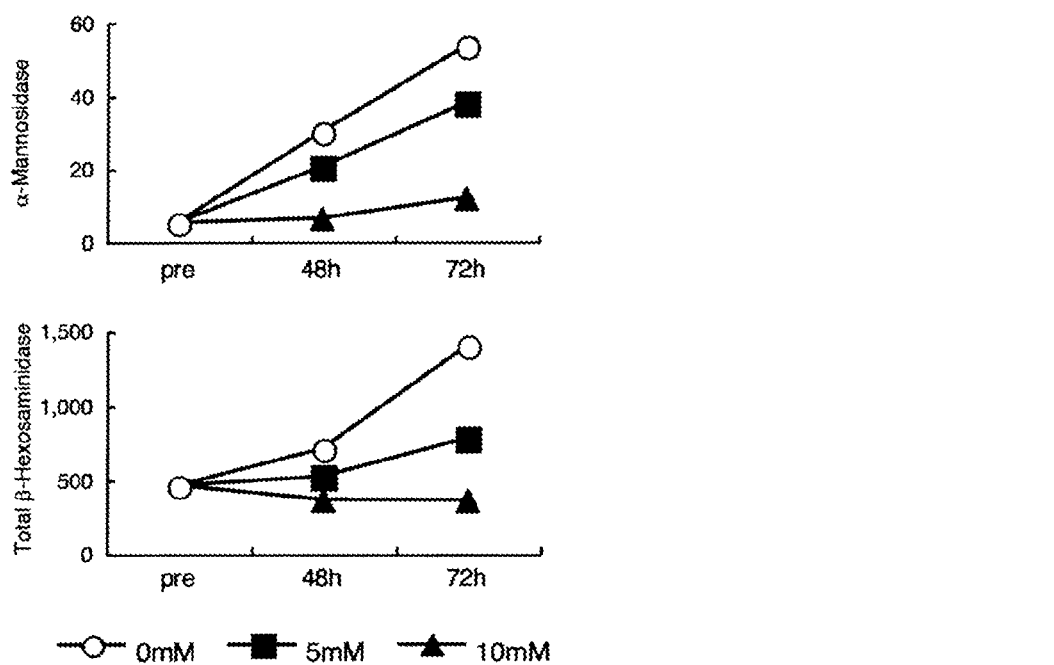
Figures 2, 4:
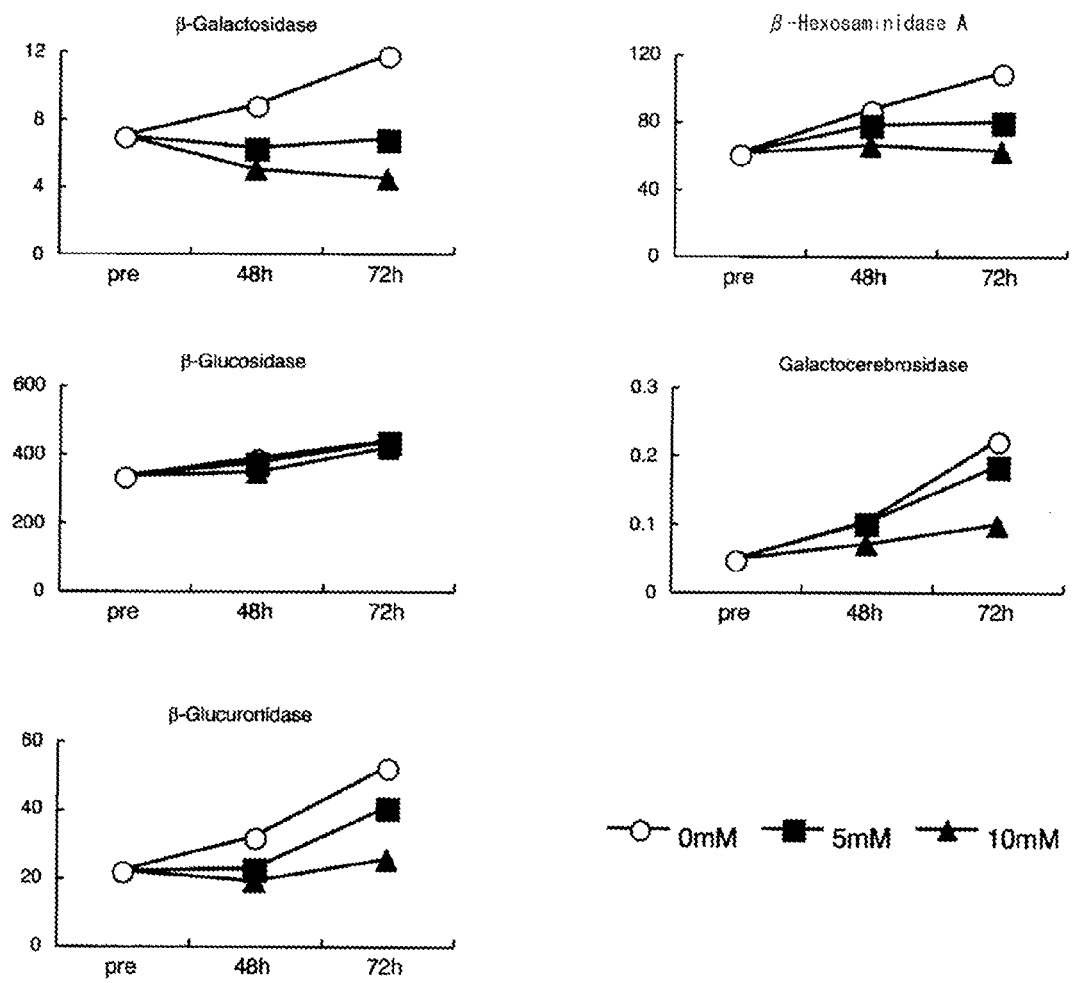

Results are shown in FIG. 4.

The intracellular uptake of lysosomal enzymes was concentration-dependently and competitively inhibited by mannose 6-phosphate.

Example 4

Confirmation of Transport of Lysosomal Enzyme Group to Lysosome

To confirm that lysosomal enzymes taken up by a cell was transported to a lysosome, immunostaining of the cell was performed.

An ML-II cell was treated with tERT as described in Example 1, and then fluorescently stained according to the following method. As controls, a normal skin fibroblast, and an ML-II cell that was not treated with tERT were used.

The cells were fixed in 3.7% formaldehyde for 1 hour followed by permeabilization with 0.1% Triton-X100 for 15 minutes and blocking with 1% bovine serum albumin at room temperature for 1 h. As a first antibody, a monoclonal anti-Lamp-2 antibody (H4B4), a polyclonal anti-cathepsin B antibody (S-12), a polyclonal anti-cathepsin D antibody (H-75), or a polyclonal anti-β-glucosidase antibody (H-300) (all purchased from Santa Cruz Biotech. Inc., Santa Cruz, Calif., USA) was used at the concentration of 1:100, and the cells were treated with the first antibody at room temperature for 1 hour. Then, a second antibody (Alexa Fluor 488 or 555, Invitrogen) was used at the dilution ratio of 1:1000, and the cells were treated with the second antibody at room temperature for 1 hour. The cells were treated with LysoTracker Red DND-99 (Molecular Probes Inc. #7528) at 0.2 µM and at 37° C. for 1 hour. All fluorescence images were acquired using a fluorescence microscope (BX51, Olympus) or confocal laser scan microscopy system (Leica TCS SP-2, Leica Microsystems). As lysosome markers, Lamp-2 and LysoTracker were used.

Figure 6:
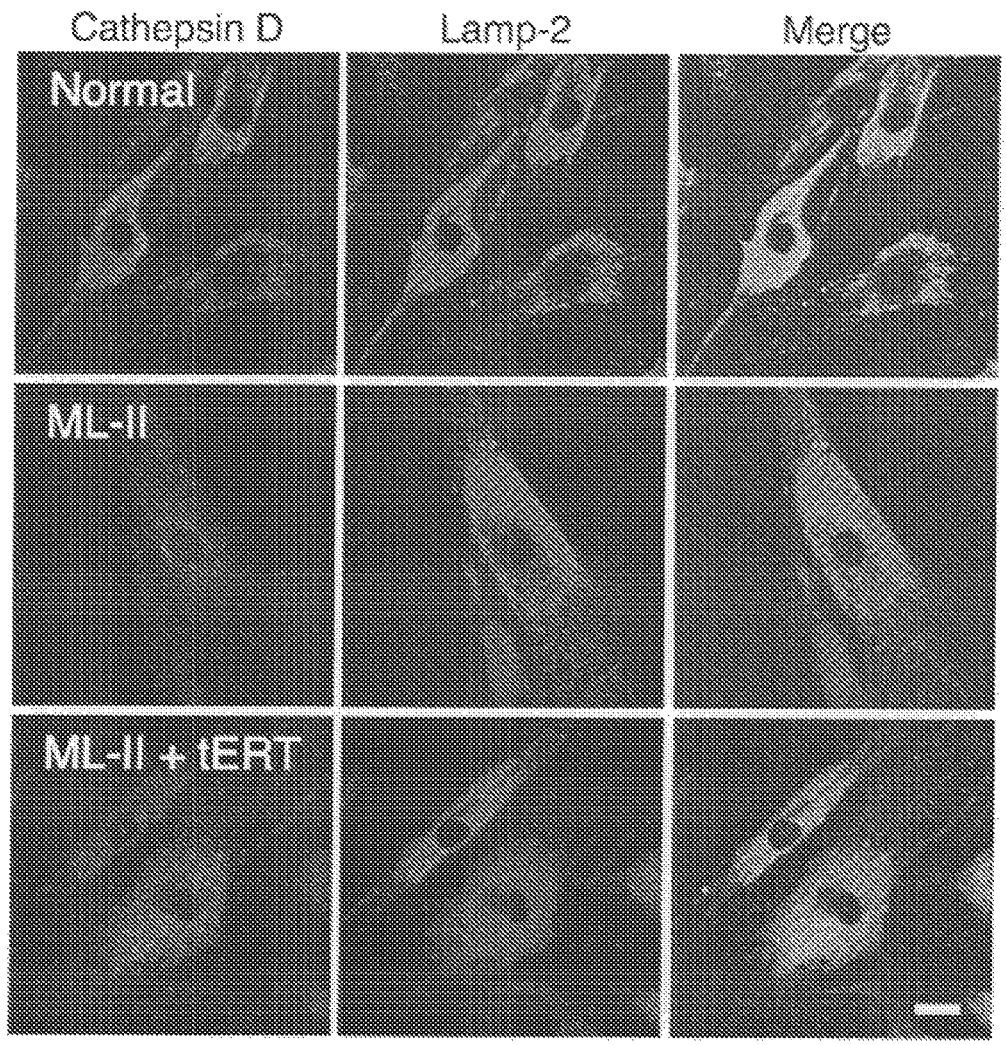
FIG. 6 displays fluorescence micrographs showing intracellular distribution of lysosomal enzymes. "Lamp-2" means a marker for lysosome. "Merge" shows images obtained by laying an image of cathepsin D on an image of Lamp-2. "ML-II+tERT" means a cell from an ML-II patient which is treated with tERT.

Results are shown in FIGS. 5 and 6.

As seen from FIGS. 5 and 6, cathepsin B and cathepsin D were not found in ML-II cells. On the other hand, in tERT-treated ML-II cells, the images of cathepsin B and cathepsin D coincided with the images of lysosome (Lamp-2). Thus, it was found that the lysosomal enzymes were transported to lysosomes from the mixture of lysosomal enzymes administered to the cell.

In the case of β-glucosidase, there was no difference in results of immunostaining among a normal cell, an ML-II cell and a tERT-treated ML-II. In addition, β-glucosidase was found to be normal in the enzyme activity test (see FIG. 2) and not to be affected in the mannose 6-phosphate competitive inhibition test (see FIG. 4).

Among lysosomal enzymes, β-glucosidase has been proved to be transported to lysosomes by not a mannose 6-phosphate-dependent transport system but LIMP-2 protein (Reczek D. et al., Cell 2007; 131 (4): 770-83). Therefore, ML-II cells do not have a deficiency of β-glucosidase. This previous finding is consistent with the experimental results as described above.

Example 5

Effect of tERT on Accumulated Substance

In ML-II, phospholipid and cholesterol are accumulated. Thus, the effect of tERT on ML-II was evaluated by measurement of the amounts of phospholipid and cholesterol in a cell.

An ML-II cell was treated with tERT as described in Example 1. Then, the amounts of phospholipid and cholesterol in the cell were measured by use of commercially available measurement kits according to the manufacturer's instructions (phospholipid: Phospholipids C-test, Wako Pure Chemicals. Co.; and cholesterol: Amples Red Cholesterol Assay Kit (A12216), Molecular Probes, Invitrogen). As controls, a normal skin fibroblast, and an ML-II cell that was not treated with tERT were used.

Figure 7:
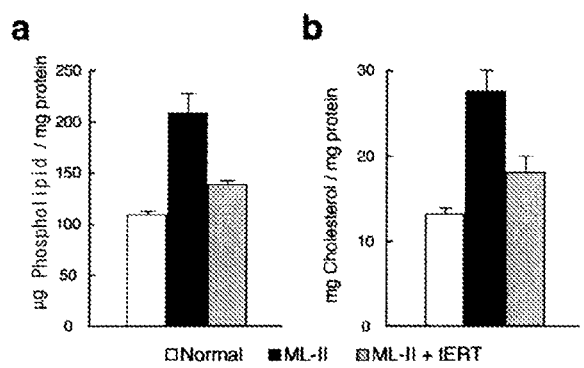
FIG. 7 shows the amounts of phospholipid (FIG. 7a) and cholesterol (FIG. 7b) accumulated in a cell. "Normal" means a normal cell. "ML-II" means a cell from a patient with ML-II. "ML-II+tERT" means a cell from an ML-II patient which is treated with tERT.

Results are shown in FIG. 7a and FIG. 7b.

Phospholipid and cholesterol were more accumulated in the ML-II cells as compared with the normal skin fibroblast. However, the tERT treatment decreased the amounts of phospholipid and cholesterol.

Example 6

Effects on Autophagic Abnormality and Mitochondrial Abnormality

The effects of tERT on autophagic abnormality and mitochondrial abnormality in ML-II were evaluated. As controls, a normal skin fibroblast, and an ML-II cell that was not treated with tERT were used.

An ML-II cell was treated with tERT as described in Example 1. Then, the amount of LC3-II in the cell was measured by western blotting. As a first antibody, a polyclonal anti-LC3 antibody (PM036) (MBL Co. Ltd., Nagoya, Japan) or a polyclonal anti-β-actin HRP DirecT antibody (PM053-7) (MBL Co. Ltd., Nagoya, Japan) was used.

Figure 8:
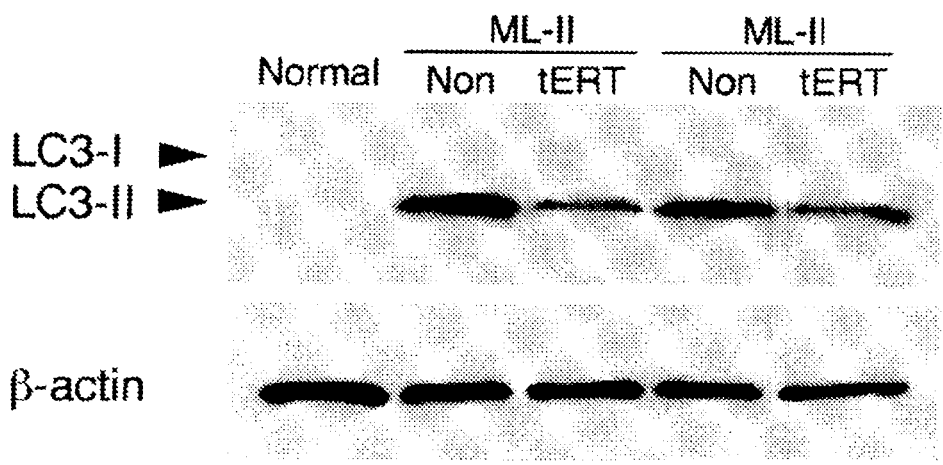
FIG. 8 is a photograph showing results of western blotting of LC3. "Normal" means a normal cell, "Non" means a cell from an ML-II patient which is not treated with tERT, and "tERT" means a cell from an ML-II patient which is treated with tERT.

Results are shown in FIG. 8. The tERT treatment decreased the amount of LC3-II.

In addition, fluorescent immunostaining was performed as described in Example 4. As a marker for mitochondria, MitoTracker Red CMXRos (Molecular Probes Inc. #7512) was used at the concentration of 200 nM, at 37° C. for 1 hour. As a marker for autophagy, a polyclonal anti-LC3 antibody (PM036) (MBL Co. Ltd., Nagoya, Japan) was used.

When observed with a fluorescence microscope, it was found that the tERT treatment decreased vesicles having LC3 and clearly improved the forms of mitochondria.

Example 7

Measurement of Number and Appearance of Lysosome

ML-II is characterized by the presence of an inclusion body in a skin fibroblast. Formation of the inclusion body is caused by accumulation in lysosomes of substrates that cannot be degraded due to abnormality of lysosomal enzymes, and at the same time, the number of lysosomes remarkably increases. The effects of tERT on these phenomena were evaluated by the following methods. As controls, a normal cell, and an ML-II cell that was not treated with tERT were used.

An ML-II cell was treated with tERT as described in Example 1. Then, the cell was harvested with trypsin by a standard method and placed in a small tube. A pellet of the cell was resuspended in a standard culture medium containing both LysoTracker Red DND-99 (1 μM) and DAPI (1 μg/ml), and incubated at 37° C. for 1 hour. After the incubation, the cell was collected by centrifugation, rinsed with PBS once, and then resuspended in PBS. The fluorescent intensity of the cell suspension was measured with a microplate reader (Corona Fluorescence Microplate Reader MTP810Lab) at excitation 530 nm/emission 590 nm (for LysoTracker) and excitation 365 nm/emission 450 nm (for DAPI). Fluorescent images were acquired in the same manner as in Example 4. As a result of the fluorescent immunostaining, it was found that the tERT treatment decreased the staining of lysosomes.

In addition, the intensity ratio of LysoTracker/DAPI was calculated, and thereby the amount (number and size) of lysosomes in each cell was evaluated.

Figure 9:
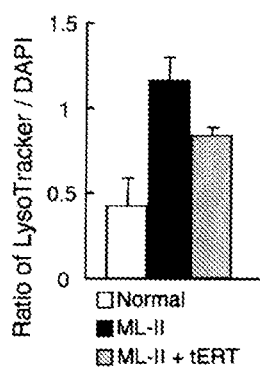
FIG. 9 is a graph showing ratios of fluorescence intensity at LysoTracker/DAPI.

Results were shown in FIG. 9. The tERT treatment decreased the amount of lysosomes in each cell.

Figure 10:
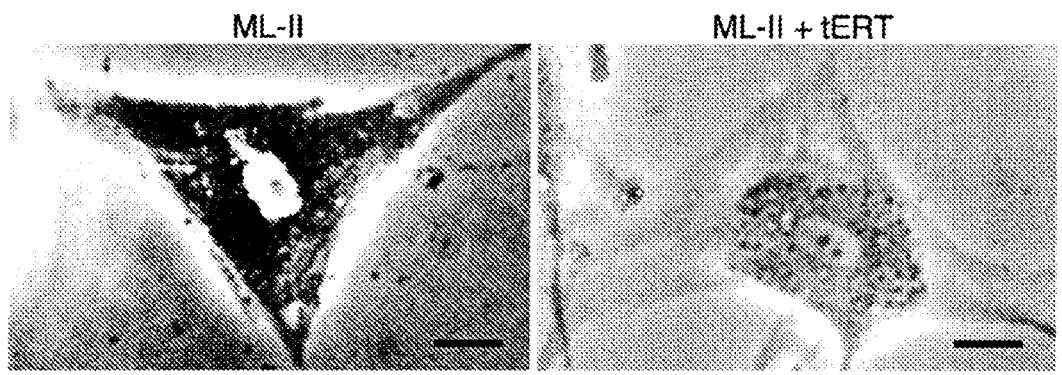
FIG. 10 shows optical micrographs of a cell from a ML-II patient ("ML-II") and a cell from a ML-II patient after treated with tERT ("ML-II+tERT").

In addition, on optical micrographs, it was found that the tERT treatment decreased the number of inclusion bodies (FIG. 10). In addition, on electron micrographs, it was found that the tERT treatment removed the accumulation of homogeneous vesicles.

Example 8

Effect on Endocytosis

A fluorescent-labeled ceramide (BODIPY-Cer) was used to evaluate intracellular transport of substances that were taken up via endocytosis by a normal cell, an ML-II cell, and a tERT-treated ML-II cell.

Skin fibroblasts were prepared in glass bottom dishes. BODIPY FL C5-ceramide complexed to BSA (Invitrogen #B22650) was purchased, and diluted at the concentration of 2.5 nM in a standard culture medium. The cells were cultured in the medium for 30 minutes. After the culture, the cells were washed once with PBS, and directly observed with the confocal microscopy described in Example 4. Fluorescent images were acquired in the same manner as in Example 4.

As a result of analysis of the fluorescent images, ceramides were transported to the Golgi body in the normal cell, whereas ceramides were enclosed inside vesicles in cytoplasm in the ML-II cell. In the case of the tERT-treated ML-II cell, ceramides were transported to the Golgi body, though a small quantity of ceramides remained inside vesicles in cytoplasm.

The attachment of BODIPY-Cer to a plasma membrane in a ice cold medium was also tested. As a result, there was no difference among the normal cell, the ML-II cell and the tERT-treated ML-II cell.

Example 9

Mannose 6-Phosphate Receptor Uptake Test

An antibody against a mannose 6-phosphate receptor was used to evaluate intracellular transport of the antibody that was taken up via the receptor on the cell surface.

Cells were incubated in a standard culture medium containing a mannose 6-phosphate receptor antibody [a monoclonal anti-mannose 6-phosphate receptor antibody (2G11) (Abcam)] at the concentration of 1:75. For a 30 minute-uptake test, cells were incubated in the antibody-containing medium for 30 minutes. After the incubation, the cell were washed with ice cold PBS and quickly fixed in 3.7% formaldehyde. The cells were permeabilized with 0.1% Triton-X100 for 15 minutes, blocked with 1% bovine serum albumin at room temperature for 1 hour, and then treated with a second antibody. For a 1 hour-uptake and 2 hour-incubation test, cells were incubated in the antibody-containing medium for 1 hour, washed, and then cultured in a standard culture medium without the antibody. The subsequent steps were the same as those for the 30 minute-uptake test as described above. As the second antibody, an Alexa Flour 488-labeled antibody (Life Technologies Corp.) was used. Fluorescent images were acquired in the same manner as in Example 4.

As a result of analysis of the fluorescent images, the antibody mannose 6-phosphate receptor antibody was accumulated in vesicles in a normal cell, whereas it was accumulated in the Golgi body in an ML-II cell. On the other hand, a tERT-treated ML-II cell showed the same pattern of vesicles as that in the normal cell.

Example 10

Preparation of Lysosomal Enzyme Group Using Various Reagents

In a culture dish with a diameter of 10 cm, a normal skin fibroblast was cultured in a standard culture medium until the cell became confluent. To the cultured normal skin fibroblast, ammonium chloride was added in such an amount that the concentration became 20 mM in the culture medium, chloroquine was added in such an amount that the concentration became 20 μM in the culture medium, or bafilomycin A1 was added in such an amount that the concentration became 20 nM in the culture medium. Then, the cell was cultured. Five days after and 7 days after, a culture supernatant was collected, and filtered with a 0.2 μm sterilizing filter to remove large debris and living cells. After the filtration, the activities of lysosomal enzymes contained in the supernatant were measured by the same method as described in Example 1. As a control, a culture supernatant of a normal skin fibroblast that was cultured in a standard culture medium with no addition of any reagents was used to measure the activities of lysosomal enzymes in the culture supernatant.

Results are shown in Tables 1 and 2. In Tables 1 and 2, β-Gal means β-galactosidase, total β-Hex means total β-hexosaminidase, β-Hex A means β-hexosaminidase A, β-Gluc means β-glucosidase, α-Man means α-mannosidase, α-Fuc means α-fucosidase, α-Gluc means α-glucosidase, α-Gal means α-galactosidase, β-Glucuro means β-glucuronidase, α-L-Iduro means α-L-iduronidase, and GALC means galactocerebrosidase. SCM means a standard culture medium with no addition of any reagents. CQ means chloroquine. Bafilo means bafilomycin A1. The enzyme activity is expressed as nmol/h/μL.

TABLE 1

Enzyme activities in Day 5 culture supernatants of normal cell + various reagents

|  | SCM | NH$_4$Cl | CQ 20 uM | Bafilo 20 nM |
|---|---|---|---|---|
| β-Gal | 4.09 | 8.20 | 5.56 | 4.65 |
| total β-Hex | 350.0 | 736.1 | 761.0 | 437.7 |
| β-Hex A | 22.5 | 67.00 | 55.0 | 18.9 |
| β-Gluc | 3.53 | 4.53 | 3.61 | 3.97 |
| α-Man | 95.9 | 137.1 | 112.9 | 100.4 |
| α-Fuc | 2.60 | 6.68 | 7.94 | 3.49 |
| α-Gluc | 1.16 | 1.92 | 1.30 | 1.13 |

TABLE 1-continued

Enzyme activities in Day 5 culture supernatants of normal cell + various reagents

|  | SCM | NH$_4$Cl | CQ 20 uM | Bafilo 20 nM |
|---|---|---|---|---|
| α-Gal | 0 | 0 | 0 | 0 |
| β-Glucuro | 0 | 3.85 | 5.52 | 4.07 |
| α-Iduro | 0.50 | 3.61 | 2.42 | 0.57 |
| GALC | 0.55 | 0.55 | 0.60 | 0.64 |

TABLE 2

Enzyme activities in Day 7 culture supernatants of normal cell + various reagents

|  | SCM | NH$_4$Cl | CQ 20 uM | Bafilo 20 nM |
|---|---|---|---|---|
| β-Gal | 4.02 | 11.65 | 7.71 | 2.93 |
| total β-Hex | 558.8 | 1239.2 | 786.7 | 300.5 |
| β-Hex A | 41.0 | 157.9 | 161.1 | 22.5 |
| β-Gluc | 5.60 | 5.39 | 6.15 | 8.65 |
| α-Man | 104.4 | 200.0 | 167.1 | 123.9 |
| α-Fuc | 3.35 | 5.70 | 12.52 | 3.97 |
| α-Gluc | 1.19 | 4.51 | 5.63 | 2.44 |
| α-Gal | 0 | 0.84 | 3.01 | 0.91 |
| β-Glucuro | 2.33 | 12.78 | 18.00 | 8.03 |
| α-Iduro | 3.67 | 13.90 | 22.04 | 0.64 |
| GALC | 0.55 | 0.50 | 0.57 | 0.69 |

As seen from Tables 1 and 2, in the cases of using chloroquine and bafilomycin A1 as well as ammonium chloride, a group of lysosomal enzymes could be excreted in larger amounts as compared with the case where none of these reagents were added.

Example 11

Preparation of Lysosomal Enzyme Group from COS-1 Cell

In a culture dish with a diameter of 10 cm, a COS-1 cell was cultured in a standard culture medium until the cell became confluent. To the cultured COS-1 cell, ammonium chloride was added in such an amount that the concentration became 20 mM in the culture medium. Then, the cell was cultured. Three days after, a culture supernatant was collected, and filtered with a 0.2 μm sterilizing filter to remove large debris and living cells. After the filtration, the activities of lysosomal enzymes contained in the supernatant were measured by the same method as described in Example 1. As a control, a culture supernatant of a COS-1 cell that was cultured in a standard culture medium with no addition of ammonium chloride was used to measure the activities of lysosomal enzymes in the culture supernatant.

Results are shown in Table 3. In Table 3, β-Gal means β-galactosidase, total β-Hex means total β-hexosaminidase, β-Hex A means β-hexosaminidase A, β-Gluc means β-glucosidase, α-Man means α-mannosidase, α-Fuc means α-fucosidase, α-Gluc means α-glucosidase, α-Gal means α-galactosidase, β-Glucuro means β-glucuronidase, α-L-Iduro means α-L-iduronidase, and GALC means galactocerebrosidase. NH$_4$Cl(−) means a culture supernatant in the case of no addition of ammonium chloride. NH$_4$Cl(+) means a culture supernatant in the case of addition of ammonium chloride. The enzyme activity is expressed as nmol/h/μL.

TABLE 3

Day 3 culture supernatant of COS1 + NH4Cl

|  | NH$_4$Cl (−) | NH$_4$Cl (+) |
|---|---|---|
| β-Gal | 18.06 | 25.26 |
| total β-Hex | 537.2 | 799.8 |
| β-Hex A | 31.8 | 85.9 |
| β-Gluc | 10.23 | 6.64 |
| α-Man | 174.6 | 178.0 |
| α-Fuc | 11.1 | 24.2 |
| α-Gluc | 4.57 | 7.96 |
| α-Gal | 3.29 | 10.60 |
| β-Glucuro | 4.14 | 21.37 |
| α-Iduro | 4.00 | 13.60 |
| GALC | 0.34 | 0.41 |

As seen from Table 3, in the case of using a COS-1 cell, a group of lysosomal enzymes could be excreted in larger amounts by addition of ammonium chloride, as compared with the case of no addition of ammonium chloride.

Example 12 tERT Test for Krabbe Disease and Tay-Sachs Disease

The lysosomal enzyme group sample obtained in Example 1 was added to culture media of skin fibroblasts derived from a patient with Krabbe disease and a patient with Tay-Sachs disease (hereinafter, referred to as "a Krabbe disease cell" and "a Tay-Sachs disease cell" respectively), and the respective cells were cultured for 7 days. Then, the cells were isolated from the culture media, and sonicated in water containing a protease inhibitor to obtain suspensions. The protein concentration of the suspensions was measured by a conventional method. The activities of lysosomal enzymes in the suspensions were measured according to the method as described in Example 1. The enzyme activities were calculated as nmol/h/mg protein. As controls, a normal skin fibroblast, and a Krabbe disease cell that was not treated with tERT or a Tay-Sachs disease cell that was not treated with tERT were used. Results are shown in FIG. 11.

Figure 11:
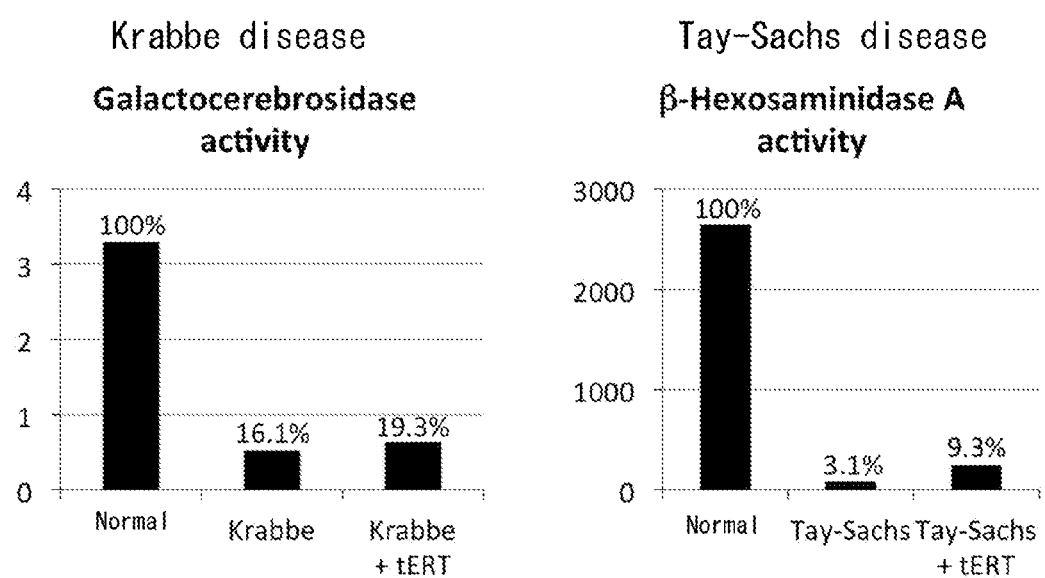
FIG. 11 displays graphs showing effects of tERT on a cell from a patient with Krabbe disease and a cell from a patient with Tay-Sachs disease. "Normal" means a normal cell. "Krabbe" means a cell from a patient with Krabbe disease. "Krabbe+tERT" means a cell from a Krabbe patient which is treated with tERT. "Tay-Sachs" means a cell from a patient with Tay-Sachs disease. "Tay-Sachs+tERT" means a cell from a Tay-Sachs patient which is treated with tERT. The unit of enzyme activity is "nmol/h/mg protein".

As seen from FIG. 11, the intracellular activities of the respective deficient lysosomal enzymes of Krabbe disease and Tay-Sachs disease (galactocerebrosidase for Krabbe disease, and β-hexosaminidase A for Tay-Sachs disease) were increased by tERT using the lysosomal enzyme group of the present invention.

The invention claimed is:

1. A process for producing a pharmaceutical composition for treating mucolipidosis type II or type III, comprising a group of purified lysosomal enzymes as an active ingredient, the process comprising obtaining the group of lysosomal enzymes by performing the following steps:
   adding to a cell one or more reagents selected from the group consisting of amphiphilic amines, lysosometropic amines, ionophores, and V-ATPase inhibitors, followed by culturing;
   collecting a culture supernatant; and
   purifying the obtained culture supernatant,
   wherein the group of purified lysosomal enzymes comprises at least α-mannosidase, α-fucosidase, α-galactosidase, α-glucosidase, β-galactosidase, β-glucosidase, β-hexosaminidase, β-glucuronidase, galactocerebrosidase, and cathepsin, and wherein the purified lysosomal enzymes are not recombinant enzymes.

2. The process according to claim 1, wherein the reagent is bafilomycin A1.

3. A process for producing a pharmaceutical composition for treating mucolipidosis type II or type III, comprising a group of purified lysosomal enzymes as an active ingredient, the process comprising obtaining the group of lysosomal enzymes by performing the following steps:
 adding to a cell one or more reagents selected from the group consisting of amphiphilic amines, lysosometropic amines, ionophores, and V-ATPase inhibitors, followed by culturing, wherein the cell is not a cell into which a gene encoding a lysosomal enzyme has been artificially integrated;
 collecting a culture supernatant; and
 purifying the obtained culture supernatant,
 wherein the group of purified lysosomal enzymes comprises at least α-mannosidase, α-fucosidase, α-galactosidase, α-glucosidase, β-galactosidase, β-glucosidase, β-hexosaminidase, β-glucuronidase, galactocerebrosidase, and cathepsin.

* * * * *